(12) United States Patent
Höflinger et al.

(10) Patent No.: US 7,523,642 B2
(45) Date of Patent: Apr. 28, 2009

(54) METHOD AND DEVICE FOR DETERMINING THE FRACTIONS OF LUBRICANTS EMITTED INTO THE ATMOSPHERE IN COOLANT PROCESSES

(75) Inventors: Wilhelm Höflinger, Vienna (AT); Peter Wlaschitz, Vienna (AT)

(73) Assignee: Palas GmbH Parikel-und Lasermesstechnik, Karlsruhe (DE)

( * ) Notice: Subject to any disclaimer, the term of this patent is extended or adjusted under 35 U.S.C. 154(b) by 251 days.

(21) Appl. No.: 11/491,422

(22) Filed: Jul. 21, 2006

(65) Prior Publication Data

US 2007/0039373 A1      Feb. 22, 2007

(30) Foreign Application Priority Data

Aug. 22, 2005    (AT)    ................... 1390/2005

(51) Int. Cl.
  *G01N 1/00*    (2006.01)
(52) U.S. Cl. .................. 73/23.41; 73/23.2; 73/28.01; 73/28.06; 73/31.07
(58) Field of Classification Search ............... 73/23.2, 73/23.41, 32; 162/198, 263, 274; 250/308; 420/15, 16; *G01N 1/00, 7/00*
See application file for complete search history.

(56) References Cited

U.S. PATENT DOCUMENTS

2003/0013606 A1 *  1/2003  Hampden-Smith et al. .. 502/180
2005/0069456 A1 *  3/2005  Dalmia et al. ................. 422/78

FOREIGN PATENT DOCUMENTS

GB    0304253.8    *  2/2003

* cited by examiner

*Primary Examiner*—Hezron Williams
*Assistant Examiner*—Mark Shabman
(74) *Attorney, Agent, or Firm*—Laurence A. Greenberg; Werner H. Stemer; Ralph E. Locher

(57) ABSTRACT

A method for determining fractions of coolants emitted into the atmosphere in processes using coolants, in particular in the metal processing industry. Here, samples of the atmosphere polluted with fractions of coolants in droplet and vapor form are fed to an evaporator. In the evaporator, the fractions of coolants in droplet form contained in the samples are evaporated and subsequently the vapor resulting from the fractions of coolants in droplet form is fed to an analysis unit, in particular a flame ionization detector, together with the fractions of coolants in vapor form contained in the samples. In the analysis unit the concentrations of the coolants contained in the samples are ascertained.

14 Claims, 2 Drawing Sheets

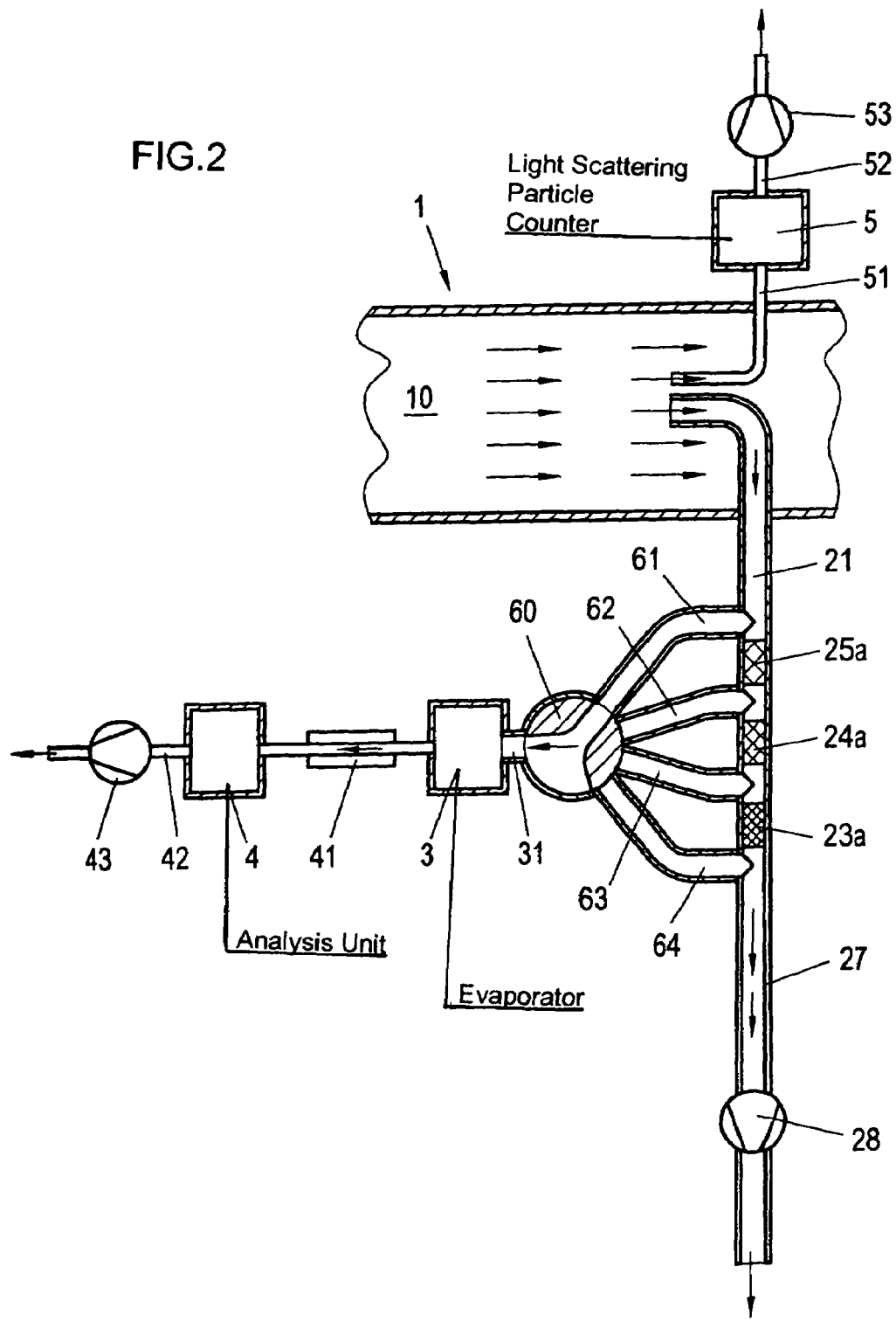

METHOD AND DEVICE FOR DETERMINING THE FRACTIONS OF LUBRICANTS EMITTED INTO THE ATMOSPHERE IN COOLANT PROCESSES

BACKGROUND OF THE INVENTION

Field of the Invention

The present invention relates to a method for determining the fractions of coolants emitted into the atmosphere in processes using coolants, in particular in the metal processing industry, and to a device for carrying out the method.

Metal processing requires the use of coolants which lubricate the contact surfaces in order to reduce friction, to dissipate the heat occurring in the processing, and also to convey away chips and the like. Mineral oils, natural oils or synthetic oils or water/oil emulsions containing from 2% to 10% of oil are used as coolants. Coolant emulsions are particularly advantageous on account of their high cooling capacity and the fact that they do not cause risk of fire or explosions.

With the use of coolants in metal processing the atmosphere is, however, polluted with fractions of coolants in droplet and vapor form emitted into the atmosphere. With respect to this pollution, standardized values for the exposure limits at the workplace apply to the concentration of fractions of coolants in droplet and vapor form, which values relate to the oil fractions and must not be exceeded. This is why the concentrations of emissions polluting the atmosphere need to be determined for different types and compositions of coolants, in different processes, under different conditions and the like, first in order to ensure that existing standards are complied with, and second in order to achieve optimizations with regard to minimizing pollution of the atmosphere when coolants are used.

It is known to determine emissions from coolants by filtering off the fractions in droplet form from samples of the atmosphere polluted by coolants via filters and by binding the fractions in vapor form by use of adsorber resins, the fractions of coolants contained in the waste air being ascertained by weighing the filters and eluting the adsorber resins and analyzing the eluate. It is, however, not possible to determine the sizes of the fractions in droplet form by these methods, notwithstanding the fact that these are complicated and time-consuming methods.

It is furthermore known to determine the number and sizes of the fractions of coolants in droplet form contained in the atmosphere using a light scattering particle counter. This method is advantageous when compared to filtration as quick results are possible. However, this method fails to meet requirements as in many respects it yields incorrect results. This is because, if the emissions of coolants which are not emulsified in water are determined, the measurement results for the fractions in droplet form emitted into the atmosphere are correct. However, only the fractions in droplet form, and not the fractions in vapor form are measured using a light scattering particle counter.

If, on the other hand, the emissions of coolants emulsified in water are to be determined, which is usually the case in view of the special advantages of coolant emulsions, this method not only has the disadvantage that the fractions in vapor form are not detected, but this method has the further disadvantage that only the number and sizes of the fractions in droplet form are detected. But no statements can be made with regard to the amounts of coolants in volume units, since the fractions in droplet form contain different contents of coolants.

SUMMARY OF THE INVENTION

It is accordingly an object of the invention to provide a method and a device for determining the fractions of lubricants emitted into the atmosphere in coolant processes that overcome the above-mentioned disadvantages of the prior art methods and devices of this general type, by which a total content of coolants contained in one volume unit in the samples as fractions in droplet and vapor form can be measured, and in which the measurement result is available quickly.

According to the invention, the objects are achieved in that the samples of the atmosphere polluted with fractions of coolants in droplet and vapor form are fed to an evaporator. In the evaporator, fractions of coolants in droplet form contained in the samples are evaporated and in that subsequently the vapor resulting from the fractions of coolants in droplet form is fed to an analysis unit, in particular a flame ionization detector, together with the fractions of coolants in vapor form contained in the samples. The analysis unit then determines the concentrations of the coolants contained in the samples.

Preferably the number of hydrocarbon atoms contained in volume units of the samples is determined in the analysis unit. Furthermore it is preferred to heat the samples in the evaporator to 300° C. to 400° C., as a result of which the fractions of coolants in droplet form contained therein are evaporated, whereupon the samples are fed to the analysis unit, in particular the flame ionization detector, at a temperature of approximately 300° C.

The method makes it possible to quickly check samples of atmosphere loaded with coolants for the amounts of the fractions of coolants contained therein. The measurement results being independent of whether the fractions are fractions of coolants in droplet or vapor form, and it furthermore being irrelevant whether the samples involved are pure coolants (not mixed with water) or coolant emulsions.

It is not possible, however, to use the method to determine the sizes of the fractions of coolants in droplet form contained in the polluted atmosphere. If the fractions in droplet form need to be determined according to their size as well, the fractions of coolants in droplet form contained in the samples are furthermore fractionated according to their sizes and the fractions of the samples, which fractions are fractionated according to their sizes, are fed to the evaporator. In this case, fractionation of the fractions according to size can take place using so-called impactors.

According to the method, in each case those fractions in droplet form which exceed a respectively prespecified size can be separated out in successive steps from the samples of the atmosphere polluted with coolants, whereby in a first step only those fractions in droplet form which do not exceed a certain size and the fractions of coolants in vapor form contained in the relevant sample are detected. In further steps, in each case the fractions in droplet form up to the respective maximum size and the fractions in vapor form are detected. The contents of fractions of coolants in droplet form in the relevant sample in certain size ranges can be detected by subtracting the measurement values obtained in the respectively preceding steps.

In a final step, a sample which contains all fractions of coolants in droplet and vapor form contained in the sample is fed to the evaporator and the analysis unit. The amounts of the fractions in droplet form in the relevant size ranges can be ascertained by subtracting the measurement values ascertained in the respectively preceding steps. In order to detect the fractions of coolants in vapor form in the samples in the best possible manner, the lowermost size of the fractions in droplet form is selected to be as small as possible.

Preferably the samples are fed to the evaporator on the one hand, and the light scattering particle counter on the other hand, as a result of which it is also possible to ascertain the size distribution of the fractions in droplet form.

A device according to the invention for carrying out the process has an evaporator and an analysis unit, in particular a flame ionization detector, to which samples of the atmosphere polluted with coolants can be fed. Preferably a blower for conveying the samples is provided. According to a further preferred embodiment, a plurality of apparatuses for fractionating the samples according to prespecified sizes of the fractions of coolants in droplet form are located upstream of the evaporator, it being possible for only one specific sample to be fed to the evaporator by a control device. Preferably, a light scattering particle counter is additionally provided. Preferably the evaporator is furthermore connected to the analysis unit, in particular the flame ionization detector, via a heated line.

Other features which are considered as characteristic for the invention are set forth in the appended claims.

Although the invention is illustrated and described herein as embodied in a method and a device for determining the fractions of lubricants emitted into the atmosphere in coolant processes, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 2 is a diagrammatic illustration of a second embodiment of the device for determining fractions of lubricants emitted into the atmosphere in coolant processes according the invention.

DESCRIPTION OF THE PREFERRED EMBODIMENTS

Figure 1:
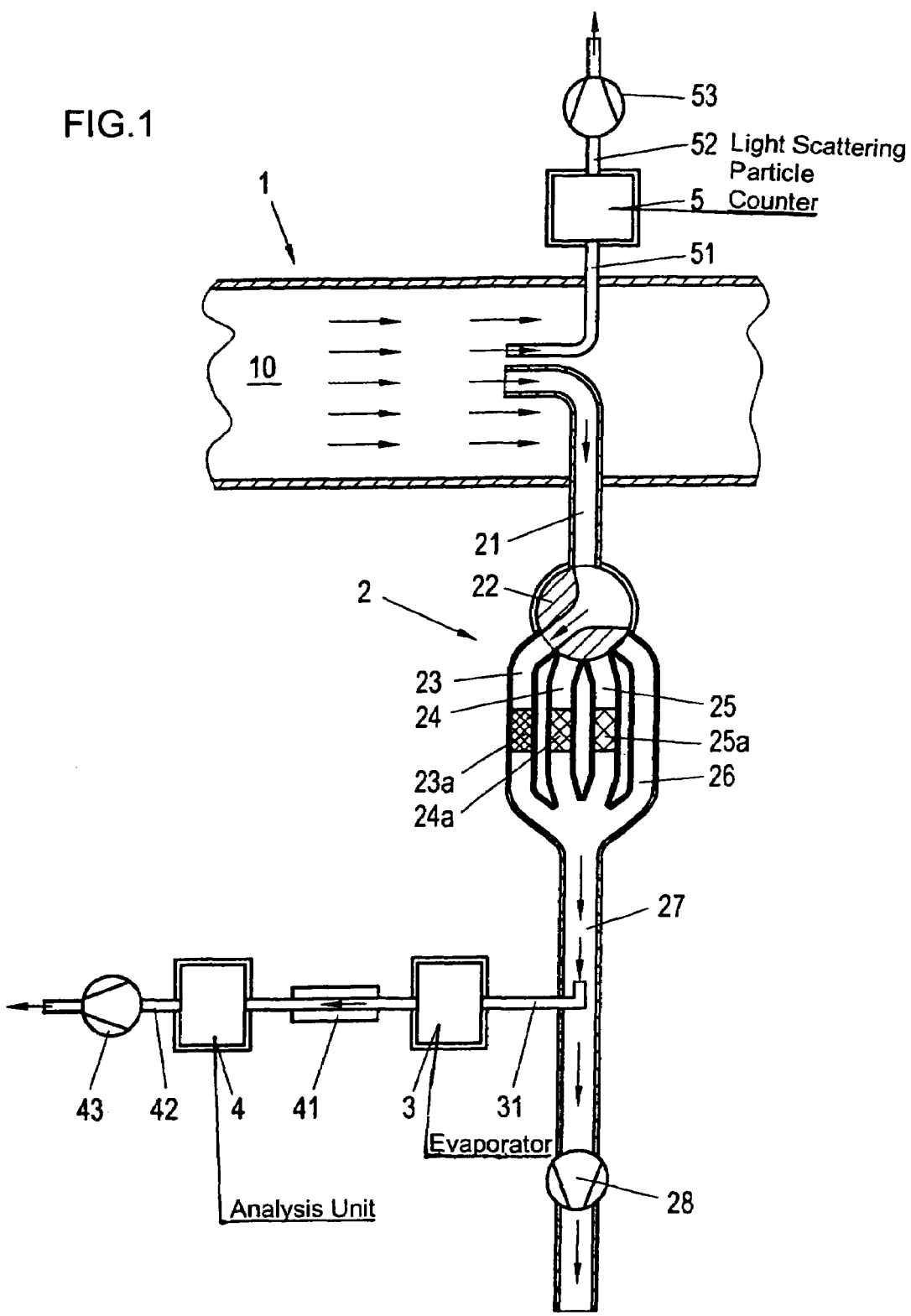
FIG. 1 is a diagrammatic illustration of a first embodiment of a device for determining fractions of lubricants emitted into the atmosphere in coolant processes according the invention.

Referring now to the figures of the drawing in detail and first, particularly, to FIG. 1 thereof, there is shown a line 21 leading to an apparatus 2 for fractionating fractions of coolants in droplet form according to their sizes. The line 21 projects into an interior 10 of a channel 1, in which waste air polluted with fractions of coolants in droplet and vapor form flows. The apparatus 2 has a plurality of parallel channels 23, 24, 25 and 26 through which samples of the waste air polluted with fractions of coolants in droplet and vapor form are introduced, as desired, via the line 21 by a control device 22 located upstream of the apparatus 2. In the channels 23, 24 and 25 there are apparatuses 23a, 24a and 25a, by which the fractions of coolants in droplet form contained in the samples are fractionated based on their sizes. By way of example, all fractions in droplet form whose diameter exceeds the value of 0.3 μm are removed via apparatus 23a, all fractions in droplet form whose diameter exceeds the value of 1 μm are removed via apparatus 24a, and all fractions in droplet form whose diameter exceeds the value of 2 μm are removed via apparatus 25a. These apparatuses contain, for example, so-called impactors.

By contrast, all fractions of coolants in droplet and vapor form contained in the relevant sample pass through channel 26. Channels 23, 24, 25 and 26 issue in line 27 where the waste air polluted with fractions of coolants in droplet and vapor form is discharged by a blower 28.

A line 31 projects into an interior of line 27, which line 31 leads to an evaporator 3. A heated line 41 leads from the evaporator 3 to an analysis unit 4 which contains, for example, a flame ionization detector. A line 42 in which a blower 43 is situated follows the analysis unit 4. A line 51 leading to a light scattering particle counter 5 projects into the channel 1. A line 52 in which another blower 53 is situated branches off from the light scattering particle counter 5.

The method of operation of the device is now described. Samples of the waste air polluted with fractions of coolants in droplet and vapor form are taken, via line 21, by use of the blower 28 from channel 1 in which the waste air flows. The samples are guided through one of the channels 23, 24, 25 and 26 of apparatus 2 by the control device 22. The apparatuses 23a, 24a and 25a for fractionating the fractions of coolants in droplet form contained in the samples are situated within the channels 23, 24 and 25.

All fractions of coolants in droplet form whose diameter is larger than 0.3 μm are removed via apparatus 23a, by way of example.

All fractions in droplet form whose diameter is larger than 1 μm are removed via apparatus 24a, by way of example.

All fractions in droplet form whose diameter is larger than 2 μm are removed via apparatus 25a, by way of example.

By contrast, all fractions of coolants in droplet and vapor form contained in the samples pass through channel 26.

Furthermore, fractions of the samples are fed to the evaporator 3 via line 31 by the blower 43, in which evaporator the fractions of coolants in droplet form contained in these samples are evaporated at a temperature of approximately 300° C. to 400° C. The outlet of the evaporator 3 is guided via the line 41, which is preferably heated, to the analysis unit 4 for determining the amounts of hydrocarbon contained in the samples.

If a sample contained in the waste air is guided through channel 26 in apparatus 2, it contains both the fractions of coolants in droplet form and the fractions in vapor form. The analysis unit 4 detects all hydrocarbon atoms, irrespective of whether they were contained in the sample in the liquid or the gaseous phase. Thus the loading of the atmosphere with the fractions of coolants finding their way into the atmosphere on account of coolant processes is determined this way.

If it is also to be determined what size distribution the fractions in droplet form have and to what extent the fractions in droplet form, on the one hand, and the fractions in vapor form, on the other hand, of the coolants are contained in the samples, samples taken from the waste air are successively passed through the channels 23, 24 and 25, the fractions in droplet form contained in the samples being fractionated according to their sizes.

Since only those fractions of coolants in droplet form whose diameter is less than 0.3 μm pass through the channel 23 into the evaporator 3, the content of coolants contained in those fractions in droplet form whose diameter is less than 0.3 μm and in the fractions in vapor form in the relevant sample can be determined in this way.

Since only those fractions of coolants in droplet form whose diameter is less than 1 μm and the respective fractions in vapor form pass through the channel 24 into the evaporator 3, and only those fractions of coolants in droplet form whose diameter is less than 2 μm and the respective fractions in vapour form pass through the channel 25 into the evaporator 3, it is possible to carry out a corresponding analysis in this way.

All fractions of coolants in droplet and vapor form pass through channel 26.

Thus the fractions of coolants in vapor form in the samples, on the one hand, and the contents of the fractions of coolants in droplet form with diameters of less than 0.3 μm, from 0.3 μm to 1 μm, from 1 μm to 2 μm and of more than 2 μm can be ascertained by subtracting the measurement results of the respectively preceding samples. This way it is furthermore possible to ascertain, on the one hand, the fractions of coolants in vapor form on their own, and, on the other hand, all the fractions of coolants in droplet form on their own.

In order to detect the fractions of coolants in vapor form, the lowermost threshold value is selected to be as small as possible. By way of example, the lowermost threshold value can lie in the range from 0.1 μm to 0.5 μm.

If the size distributions of the fractions of coolants in droplet form in the samples are also to be ascertained, fractions of the samples are fed, via line 51, by a fan 53 to a light scattering particle counter 5. This makes it possible for the size distributions of the fractions of coolants in droplet form in the individual samples to be ascertained and for them to be related to the measurement results obtained by the analysis unit 4.

FIG. 2 illustrates a second embodiment variant of the device according to the invention. Here, the impactor 25a, via which those fractions in droplet form whose diameters are larger than 2 μm are removed, also the impactor 24a, via which those fractions in droplet form whose diameters are larger than 1 μm are removed, and the impactor 23a, via which those fractions in droplet form whose diameters are larger than 0.3 μm are removed, are disposed successively in line 21.

Lines 61, 62, 63 and 64 leading to a control device 60 branch off of line 21, by which the samples passing through lines 61 to 64 are fed to the evaporator 3 and the analysis unit 4, which results in the evaluations.

The method of operation here is as described with reference to FIG. 1.

This application claims the priority, under 35 U.S.C. §119, of Austrian application A 1390/2005, filed Aug. 22, 2005; the prior application is herewith incorporated by reference in its entirety.

We claim:

1. A method for determining fractions of coolants emitted into an atmosphere in processes using coolants, including metal processing industries, which comprises the steps of:
feeding samples of the atmosphere polluted with the fractions of coolants in droplet and vapor form to an evaporator;
fractionating the fractions of coolants in droplet form contained in the samples according to prespecified sizes, and separately feeding each of the fractions of coolants in droplet form, which have been fractionated according to their sizes, to the evaporator;
evaporating, in the evaporator, the fractions of coolants in droplet form contained in the samples;
subsequently feeding a vapor resulting from the fractions of coolants in droplet form to an analysis unit together with the fractions of coolants in vapor form contained in the samples; and
ascertaining, in the analysis unit, concentrations of the coolants contained in the samples.

2. The method according to claim 1, which further comprises determining a number of hydrocarbon atoms contained in volume units of the samples in the analysis unit.

3. The method according to claim 1, which further comprises:
heating the samples to 300° C. to 400° C. in the evaporator, as a result of which, the fractions of coolants in droplet form contained therein are evaporated; and
feeding the samples to the analysis unit at a temperature of approximately 300° C.

4. The method according to claim 1, which further comprises determining a content of the fractions of coolants in droplet form in a prespecified size range by subtracting results of measurements of preceding ranges with smaller sizes from measurement result.

5. The method according to claim 1, which further comprises determining a content of the fractions of the coolants in vapor form as a result of the fact that a lowermost value in a fractionation of the fractions of the coolants in droplet form lies in a range of from 0.1 μm to 0.5 μm.

6. The method according to claim 4, which further comprises fractionating the fractions of coolants in droplet form according to size using impactors.

7. The method according to claim 1, which further comprises feeding the samples to the evaporator and to a light scattering particle counter.

8. The method according to claim 1, which further comprises providing a flame ionization detector as the analysis unit.

9. The method according to claim 3, which further comprises providing a flame ionization detector as the analysis unit.

10. A device for determining fractions of coolants emitted into an atmosphere in processes using coolants, the device comprising:
an evaporator receiving samples of the atmosphere polluted with the fractions of coolants in droplet and vapor form;
an analysis unit disposed downstream of said evaporator and receiving the samples after being processed in said evaporator;
a control device disposed upstream of said evaporator; and
a plurality of apparatuses for fractionating the samples according to prespecified sizes of the fractions of coolants in droplet form and disposed upstream of said evaporator, it being possible for only one specific sample to be fed to said evaporator by use of said control device.

11. The device according to claim 10, further comprising:
a line for conveying the samples to said evaporator; and
a blower for conveying the samples through said line.

12. The device according to claim 10, further comprising a light scattering particle counter.

13. The device according to claim 10, further comprising a heated line connecting said evaporator to said analysis unit.

14. The device according to claim 10, wherein said analysis unit is a flame ionization detector.

* * * * *